US008232055B2

(12) United States Patent
Bruhn et al.

(10) Patent No.: US 8,232,055 B2
(45) Date of Patent: Jul. 31, 2012

(54) COMPARATIVE GENOMIC HYBRIDIZATION ASSAYS USING IMMOBILIZED OLIGONUCLEOTIDE FEATURES AND COMPOSITIONS FOR PRACTICING THE SAME

(75) Inventors: Laurakay Bruhn, Mountain View, CA (US); Alicia F. Scheffer, Redwood City, CA (US); Michael T. Barrett, Mountain View, CA (US); Douglas A. Amorese, Los Altos, CA (US); Stephen S. Laderman, Menlo Park, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 256 days.

(21) Appl. No.: 10/744,595

(22) Filed: Dec. 22, 2003

(65) Prior Publication Data

US 2004/0191813 A1 Sep. 30, 2004

Related U.S. Application Data

(60) Provisional application No. 60/436,053, filed on Dec. 23, 2002.

(51) Int. Cl.
*C12Q 1/68* (2006.01)
*G01N 33/50* (2006.01)

(52) U.S. Cl. ........................................ 435/6.11; 702/20

(58) Field of Classification Search ........................ None
See application file for complete search history.

(56) References Cited

U.S. PATENT DOCUMENTS 5,348,855 A 9/1994 Dattagupta et al.
5,447,841 A 9/1995 Gray et al.
5,474,796 A * 12/1995 Brennan ...................... 427/2.13
5,635,351 A 6/1997 Feuerstein et al.
5,663,319 A 9/1997 Bittner et al.
5,665,549 A 9/1997 Pinkel et al.
5,690,894 A * 11/1997 Pinkel et al. ................ 422/68.1
5,721,098 A 2/1998 Pinkel et al.
5,776,688 A 7/1998 Bittner et al.
5,830,645 A 11/1998 Pinkel et al.
5,856,097 A 1/1999 Pinkel et al.
5,965,362 A 10/1999 Pinkel et al.
5,976,790 A 11/1999 Pinkel et al.
6,057,100 A * 5/2000 Heyneker .......................... 435/6
6,159,685 A 12/2000 Pinkel et al.
6,197,501 B1 3/2001 Cremer et al.
6,210,878 B1 4/2001 Pinkel et al.
6,251,601 B1 6/2001 Bao et al.
6,309,822 B1 10/2001 Fodor et al.
6,335,167 B1 1/2002 Pinkel et al.
6,365,353 B1 4/2002 Lorch et al.
6,465,182 B1 10/2002 Gray et al.
6,468,744 B1 10/2002 Cronin et al.
6,562,565 B1 5/2003 Pinkel et al.
6,699,710 B1 3/2004 Kononen et al.
6,916,621 B2 * 7/2005 Shah ................................ 435/6
2002/0006622 A1 1/2002 Bradley et al.
2002/0028460 A1 3/2002 Pinkel et al.
2002/0119448 A1 8/2002 Sorge et al.
2002/0132246 A1 9/2002 Kallioniemi et al.
2003/0003496 A1 1/2003 Bradley et al.
2003/0008318 A1 1/2003 Pinkel et al.
2003/0054388 A1 * 3/2003 Garner et al. ..................... 435/6
2003/0082606 A1 5/2003 Lebo et al.
2003/0082618 A1 * 5/2003 Li et al. ............................ 435/6
2004/0009493 A1 1/2004 Mohammed et al.
2004/0063104 A1 * 4/2004 Amorese et al. ................. 435/6
2004/0081996 A1 4/2004 Landers et al.
2004/0132048 A1 7/2004 Martienssen et al.
2004/0137473 A1 7/2004 Wigler et al.
2004/0157243 A1 * 8/2004 Huang et al. ...................... 435/6
2004/0241658 A1 * 12/2004 Barrett et al. .................... 435/6
2004/0248144 A1 12/2004 Mir

FOREIGN PATENT DOCUMENTS

EP 1430153 6/2004
JP 01151068 A2 6/1989
JP 2223761 A2 9/1990
JP 02271687 A2 11/1990
JP 7505053 A1 6/1995
JP P2001-521754 A 11/2001
WO WO 9826098 6/1998
WO WO 99/23256 10/1998
WO WO 9900520 1/1999
WO WO 99/23256 5/1999
WO WO 99/23256 A1 5/1999
WO WO9923256 A1 5/1999
WO WO 0175160 10/2001
WO WO 0190416 11/2001
WO WO 02086163 10/2002
WO WO 03020898 3/2003
WO WO 03030620 4/2003
WO WO 03057923 7/2003
WO WO 2004035819 4/2004
WO WO 2004088310 10/2004
WO WO 2004111267 12/2004

OTHER PUBLICATIONS

Wells, CA and Sowter, C. 2000. "Telepathology: a diagnostic tool for the millenium?" J. of Pathology. vol. 191, p. 1-7.* Crossen, PE et al. "Identification of amplified genes in a patient with acute myeloid leukemia and double minute chromosomes", Cancer Genet Cytogenet, 1999, 113: 126-133.*
Pollack et al. (Nature Genetics, 1999, vol. 23, p. 41-46).*
Winzeler al. (Parasitology, 1999, vol. 118, p. S73-S80).*
Zoller et al. (Chromosome Research, 2001, vol. 9, No. 5, p. 357-375).*
Pollack et al. (Nature Genetics, 1999, 23(1):41-6).*
Kallioniemi et al. "Comparative Genomic Hybridization for Molecular Cytogenic Analysos of Solid Tumors" Science (1992) 25:818-21.
Schena et al.: Quantitative Monitoring of Gene Expression Patterns with a Complementary DNA Microarray Science (1995) 270:467-470.
Schena, Mark et al., Quantitative Monitoring of Gene Expression Patterns with a Complementary DNA Microarray, Science, vol. 270, Oct. 1995, pp. 467-470.

(Continued)

*Primary Examiner* — Stephanie K Mummert

(57) ABSTRACT

Comparative genomic hybridization assays and compositions for use in practicing the same are provided. A characteristic of the subject comparative genomic hybridization assays is that solid support immobilized oligonucleotide feature elements, e.g., in the form of an array, are employed. Specifically, at least first and second nucleic acid populations prepared from genomic templates are contacted with a plurality of distinct oligonucleotide feature elements immobilized on a solid support surface and the binding of the at least first and second populations is then evaluated. Also provided are kits for use in practicing the subject methods.

42 Claims, 6 Drawing Sheets

OTHER PUBLICATIONS

Pinkel, Daniel et al., High resolution analysis of DNA copy number variation using comparative genomic hybridization to microarrays, Nature Genetics, vol. 20, Oct. 1998, pp. 207-211.

Pollack, Jonathan R. et al., Genome-wide analysis of DNA copy-number changes using cDNA microarrays, Nature Genetics, vol. 23, Sep. 1999, pp. 41-46.

Barrett, M., et al. Comparative genomic hybridization using oligonucleotide microarrays and total genomic DNA. PNAS. 2004, vol. 101, No. 51, pp. 17765-17770.

Kato-Maeda, M., et al. Comparing genomes within the species *myobacterium tuberculosis*. Genome Research. Apr. 2001, vol. 11, pp. 547-554.

Winzeler, E. A., et al. Whole genome genetic-typing in yeast using high-density oligonucleotie arrays. Parasitology. 1999, vol. 118, pp. S73-S80.

Barbara Jordan, Genome Complexity Reduction for SNP Genotyping Analysis, PNAS, Mar. 5, 2002, p. 2942-2947, vol. 99 No. 5, www.pnas.org/cgi/doi/10.1073/pnas261710699.

Japanese Office Action from Jan. 5, 2010.

Albertson, D., et al. Genomic microarrays in human genetic disease and cancer. Human Molecular Genetics. 2003, vol. 12, pp. R145-R152.

Bao, Y.P., et al. SNP identification in unamplified human genomic DNA with gold nanoparticle probes. Nucleic Acids Research. 2005, vol. 33, No. 2, pp. e15.

Beheshti, B., et al. Chromosomal localization of DNA amplifications in neuroblastoma tumors using cDNA microarray comparative genomic hybridization. Neoplasia. 2003, vol. 5, pp. 53-62.

Bignell, G., et al. High-resolution analysis of DNA copy number using oligonucleotide microarrays. Genome Research. 2004, vol. 14, pp. 287-295.

Carter, N. Methods and strategies for analyzing copy number variation using DNA microarrays. Nature Genetics. 2007, vol. 39, pp. S16-21.

Dong, S., et al. Flexible use of high-density oligonucleotide arrays for single-nucleotide polymorphism discovery and validation. Genome Research. 2001, vol. 11, pp. 1418-1424.

Gresham, D., et al. Comparing whole genomes using DNA microarrays. Nature Reviews Genetics. 2008, vol. 9, pp. 291-302.

Gunderson, K.L., et al. A genome-wide scalable SNP genotyping assay using microarray technology. Nature Genetics. 2005, vol. 37, abstract.

Huang, J., et al. Whole genome DNA copy number changes identified by high density oligonucleotide arrays. Human Genomics. 2004, vol. 1, pp. 287-299.

Iwasaki, H., et al. Accuracy of genotyping for single nucleotide polymorphisms by a microarray-based single nucleotide polymorphism typing method involving hybridization of short allele-specific oligonucleotides. DNA Research. 2002, vol. 9, pp. 59-62.

Jordan, B., et al. Genome complexity reduction for SNP genotypying analysis. PNAS. 2002, vol. 99, pp. 2942-2947.

Kennedy, G., et al. Large-scale genotyping of complex DNA Nature Biotechnology. 2003, vol. 21, No. 10, pp. 1233-1237.

Li, J. et al. Notl subtraction and Notl-specific microarrays to detect copy number and methylation changes in whole genomes. PNAS. 2002, vol. 99, No. 16, pp. 10724-10729.

Lindblad-Toh, K., et al. Loss-of-heterozygosity analysis of small-cell lung carcinomas using single-nucleotide polymorphism arrays. Nature Biotechnology. 2000, vol. 18, pp. 1001-1005.

Lucito, R., et al. Genetic analysis using genomic representations. PNAS. 1998, vol. 95, pp. 4487-4492.

Lucito, R., et al. Detecting gene copy number fluctuations in tumor cells by microarray analysis of genomic representations. Genome Research. 2000, vol. 10, pp. 1726-1736.

Lucito, R., et al. Representational oligonucleotide microarray analysis: A high-resolution method to detect genome copy number variation. Genome Research. 2003, vol. 13, pp. 2291-2305.

Matsuzaki, H., et al. Parallel genotyping of over 10,000 SNPs using a one-primer assay on a high-density oligonucleotide array. Genome Research. 2004, vol. 14, pp. 414-425.

Mei, R., et al. Genome-wide detection of allelic imbalance using human SNPs and high-density DNA arrays. Genome Research. 2000, vol. 10, pp. 1126-1137.

Pinkel, D., et al. Array comparative genomic hybridization and its applications in cancer. Nature Genetics. 2005, vol. 37, pp. S11-S17.

Primdahl, H., et al. Allelic imbalances in human bladder cancer: Genome-wide detection with high-density single-nucleotide polymorphism arrays. Journal of the Nation Cancer Institute. 2002, vol. 94, No. 3, pp. 216-223.

Syvanen, A. Accessing genetic variation: Genotyping single nucleotide polymorphisms. Nature Reviews Genetics. 2001, vol. 2, pp. 930-942.

Tsuchihashi, Z., et al. Progress in high throughput SNP genotyping methods. The Pharmacogenomics Journal. 2002, vol. 2, pp. 103-110.

Zhao, X., et al. An integrated view of copy number and allelic alterations in the cancer genome using single nucleotide polymorphism arrays. Cancer Research. 2004, vol. 64, pp. 3060-3071.

Mir, K., et al. Sequence variation in genes and genomic DNA: methods for large-scale analysis. Annual Review of Genomics and Human Genetics. 2000, vol. 1, pp. 329-360.

Pinkel et al. Nat. Genetics 91998) 20:207-11, (1998).

Pollack et al. Nat. Genetics (1999) 23:41-6.

Pollack et al. Proc. Natl. Acad. Science USA (Oct. 1, 2002) 99:12963-12968.

Baldocchi et al. "Oligonucleotide-array-based comparative genomic hybridization" The Microarray Meeting, Scottsdale, AZ Sep. 22-25, 1999.

* cited by examiner

COMPARATIVE GENOMIC HYBRIDIZATION ASSAYS USING IMMOBILIZED OLIGONUCLEOTIDE FEATURES AND COMPOSITIONS FOR PRACTICING THE SAME

CROSS-REFERENCE TO RELATED APPLICATIONS

Pursuant to 35 U.S.C. §119 (e), this application claims priority to the filing date of the U.S. Provisional Patent Application Serial No. 60/436,053 filed Dec. 23, 2002; the disclosure of which is herein incorporated by reference.

INTRODUCTION

1. Technical Field

The technical field of this invention is comparative genomic hybridization (CGH).

2. Background of the Invention

Many genomic and genetic studies are directed to the identification of differences in gene dosage or expression among cell populations for the study and detection of disease. For example, many malignancies involve the gain or loss of DNA sequences resulting in activation of oncogenes or inactivation of tumor suppressor genes. Identification of the genetic events leading to neoplastic transformation and subsequent progression can facilitate efforts to define the biological basis for disease, improve prognostication of therapeutic response, and permit earlier tumor detection. In addition, perinatal genetic problems frequently result from loss or gain of chromosome segments such as trisomy 21 or the micro deletion syndromes. Thus, methods of prenatal detection of such abnormalities can be helpful in early diagnosis of disease.

Comparative genomic hybridization (CGH) is one approach that has been employed to detect the presence and identify the location of amplified or deleted sequences. In one implementation of CGH, genomic DNA is isolated from normal reference cells, as well as from test cells (e.g., tumor cells). The two nucleic acids are differentially labeled and then simultaneously hybridized in situ to metaphase chromosomes of a reference cell. Chromosomal regions in the test cells which are at increased or decreased copy number can be identified by detecting regions where the ratio of signal from the two DNAs is altered. For example, those regions that have been decreased in copy number in the test cells will show relatively lower signal from the test DNA than the reference compared to other regions of the genome. Regions that have been increased in copy number in the test cells will show relatively higher signal from the test DNA.

In a recent variation of the above traditional CGH approach, the chromosomes to which the labeled nucleic acids are hybridized have been replaced with a collection of solid support bound nucleic acids, e.g., an array of BAC (bacterial artificial chromosome) clones or cDNAs. Such approaches offer benefits over immobilized chromosome approaches, including a higher resolution, as defined by the ability of the assay to localize chromosomal alterations to specific areas of the genome. However, these methods still have significant limitations in their ability to detect chromosomal alterations at single gene resolution (in the case of BAC clone arrays) or in non-coding regions of the genome in the case of cDNA clone arrays. In addition, array features containing longer lengths of nucleic acid sequence are more susceptible to binding cross-hybridizing sequences, where a given immobilized nucleic acid hybridizes to more than one distinct sequences in solution. This property limits somewhat the ability of these technologies to detect low level amplifications and deletions sensitively and accurately.

In an effort to address at least some of the above disadvantages associated with the use of cDNA arrays in CGH applications, the suggestion has been made to employ arrays of oligonucleotides instead of cDNA arrays. See specifically U.S. Pat. No. 6,465,182. However, while U.S. Pat. No. 6,465,182 suggests CGH methods that employ oligonucleotide arrays, it also teaches that one must reduce the complexity of the sample in order to use such arrays.

There are situations where one wishes to screen a sample of non-reduced complexity, e.g., a labeled sample whose complexity is substantially the same, if not the same, as the genomic nucleic acid source from which it has been produced. Accordingly, there is interest in the development of improved array based CGH methods, particularly methods that employ oligonucleotide arrays to screen samples of non-reduced complexity. The present invention satisfies this need.

Relevant Literature

United States Patents of interest include: U.S. Pat. Nos. 6,465,182; 6,335,167; 6,251,601; 6,210,878; 6,197,501; 6,159,685; 5,965,362; 5,830,645; 5,665,549; 5,447,841 and 5,348,855. Also of interest are published United States Application Serial No. 2002/0006622 and published PCT application WO 99/23256. Articles of interest include: Kallioniemi et al, Science (1992) 258:818-21; Pinkel et al., Nat. Genet. (1998) 20:207-11; Nat. Genet. (1999)23:41-6; and Science (1995) 270: 467470; and Pollack et al., Proc. Nat'l Acad. Sci, USA (Oct. 1, 2002) 99:12963-12968. Also of interest is the following poster abstract: Baldocchi et al., "Oligonucleotide-array-based comparative genomic hybridization," The Microarray Meeting, Scottsdale Ariz., Sep. 22-25,1999.

SUMMARY OF THE INVENTION

Comparative genomic hybridization assays and compositions for use in practicing the same are provided. A characteristic of the subject comparative genomic hybridization assays is that solid support immobilized oligonucleotide features, e.g., in the form of an array, are employed. Specifically, at least first and second nucleic acid populations prepared from different genomic sources are contacted with a plurality of oligonucleotide features immobilized on a solid support surface and the binding of the at least first and second populations is then evaluated. Also provided are kits for use in practicing the subject methods.

DEFINITIONS

Figure 1:
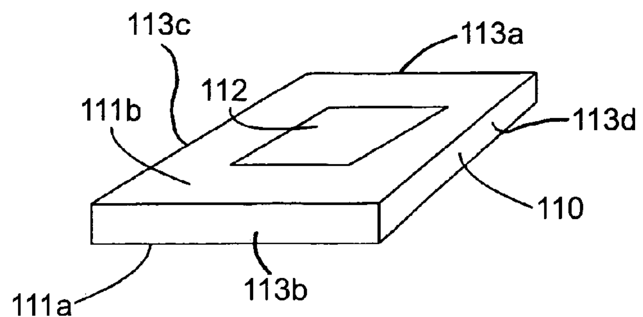
FIG. 1 shows an exemplary substrate carrying an array, such as may be used in the devices of the subject invention.

The term "oligomer" is used herein to indicate a chemical entity that contains a plurality of monomers. As used herein, the terms "oligomer" and "polymer" are used interchangeably. Examples of oligomers and polymers include polydeoxyribonucleotides (DNA), polyribonucleotides (RNA), other nucleic acids that are C-glycosides of a purine or pyrimidine base, polypeptides (proteins) or polysaccharides (starches, or polysugars), as well as other chemical entities that contain repeating units of like chemical structure.

The term "nucleic acid" as used herein means a polymer composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" as used herein denotes single stranded nucleotide multimers of from about 10 to 100 nucleotides and up to 200 nucleotides in length.

The term "functionalization" as used herein relates to modification of a solid substrate to provide a plurality of functional groups on the substrate surface. By a "functionalized surface" is meant a substrate surface that has been modified so that a plurality of functional groups are present thereon.

The terms "reactive site", "reactive functional group" or "reactive group" refer to moieties on a monomer, polymer or substrate surface that may be used as the starting point in a synthetic organic process. This is contrasted to "inert" hydrophilic groups that could also be present on a substrate surface, e.g., hydrophilic sites associated with polyethylene glycol, a polyamide or the like.

The term "sample" as used herein relates to a material or mixture of materials, typically, although not necessarily, in fluid form, containing one or more components of interest.

The terms "nucleoside" and "nucleotide" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The phrase "oligonucleotide bound to a surface of a solid support" refers to an oligonucleotide or mimetic thereof, e.g., PNA, that is immobilized on a surface of a solid substrate in a feature or spot, where the substrate can have a variety of configurations, e.g., a sheet, bead, or other structure. In certain embodiments, the collections of features of oligonucleotides employed herein are present on a surface of the same planar support, e.g., in the form of an array.

The term "array" encompasses the term "microarray" and refers to an ordered array presented for binding to nucleic acids and the like. Arrays, as described in greater detail below, are generally made up of a plurality of distinct or different features. The term "feature" is used interchangeably herein with the terms: "features," "feature elements," "spots," "addressable regions," "regions of different moieties," "surface or substrate immobilized elements" and "array elements," where each feature is made up of oligonucleotides bound to a surface of a solid support, also referred to as substrate immobilized nucleic acids.

An "array," includes any one-dimensional, two-dimensional or substantially two-dimensional (as well as a three-dimensional) arrangement of addressable regions (i.e., features, e.g., in the form of spots) bearing nucleic acids, particularly oligonucleotides or synthetic mimetics thereof (i.e., the oligonucleotides defined above), and the like. Where the arrays are arrays of nucleic acids, the nucleic acids may be adsorbed, physisorbed, chemisorbed, or covalently attached to the arrays at any point or points along the nucleic acid chain.

Any given substrate may carry one, two, four or more arrays disposed on a front surface of the substrate. Depending upon the use, any or all of the arrays may be the same or different from one another and each may contain multiple spots or features. A typical array may contain one or more, including more than two, more than ten, more than one hundred, more than one thousand, more ten thousand features, or even more than one hundred thousand features, in an area of less than 20 $cm^2$ or even less than 10 $cm^2$, e.g., less than about 5 $cm^2$, including less than about 1 $cm^2$, less than about 1 $mm^2$, e.g., 100 $\mu^2$, or even smaller. For example, features may have widths (that is, diameter, for a round spot) in the range from a 10 μm to 1.0 cm. In other embodiments each feature may have a width in the range of 1.0 μm to 1.0 mm, usually 5.0 μm to 500 μm, and more usually 10 μm to 200 μm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, 20%, 50%, 95%, 99% or 100% of the total number of features). Inter-feature areas will typically (but not essentially) be present which do not carry any nucleic acids (or other biopolymer or chemical moiety of a type of which the features are composed). Such inter-feature areas typically will be present where the arrays are formed by processes involving drop deposition of reagents but may not be present when, for example, photolithographic array fabrication processes are used. It will be appreciated though, that the inter-feature areas, when present, could be of various sizes and configurations.

Each array may cover an area of less than 200 $cm^2$, or even less than 50 $cm^2$, 5 $cm^2$, 1 $cm^2$, 0.5 $cm^2$, or 0.1 $cm^2$. In certain embodiments, the substrate carrying the one or more arrays will be shaped generally as a rectangular solid (although other shapes are possible), having a length of more than 4 mm and less than 150 mm, usually more than 4 mm and less than 80 mm, more usually less than 20 mm; a width of more than 4 mm and less than 150 mm, usually less than 80 mm and more usually less than 20 mm; and a thickness of more than 0.01 mm and less than 5.0 mm, usually more than 0.1 mm and less than 2 mm and more usually more than 0.2 and less than 1.5 mm, such as more than about 0.8 mm and less than about 1.2 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, the substrate may transmit at least 20%, or 50% (or even at least 70%, 90%, or 95%), of the illuminating light incident on the front as may be measured across the entire integrated spectrum of such illuminating light or alternatively at 532 nm or 633 nm.

Arrays can be fabricated using drop deposition from pulse-jets of either nucleic acid precursor units (such as monomers) in the case of in situ fabrication, or the previously obtained nucleic acid. Such methods are described in detail in, for example, the previously cited references including U.S. Pat.

Nos. 6,242,266, 6,232,072, 6,180,351, 6,171,797, 6,323,043, U.S. patent application Ser. No. 09/302,898 filed Apr. 30, 1999 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used. Inter-feature areas need not be present particularly when the arrays are made by photolithographic methods as described in those patents.

In certain embodiments of particular interest, in situ prepared arrays are employed. In situ prepared oligonucleotide arrays, e.g., nucleic acid arrays, may be characterized by having surface properties of the substrate that differ significantly between the feature and inter-feature areas. Specifically, such arrays may have high surface energy, hydrophilic features and hydrophobic, low surface energy hydrophobic interfeature regions. Whether a given region, e.g., feature or interfeature region, of a substrate has a high or low surface energy can be readily determined by determining the regions "contact angle" with water, as known in the art and further describedin in copending application Ser. No. 10/449,838, the disclosure of which is herein incorporated by reference. Other features of in situ prepared arrays that make such array formats of particular interest in certain embodiments of the present invention include, but are not limited to: feature density, oligonucleotide density within each feature, feature uniformity, low intra-feature background, low inter-feature background, e.g., due to hydrophobic interfeature regions, fidelity of oligonucleotide elements making up the individual features, array/feature reproducibility, and the like. The above benefits of in situ produced arrays assist in maintaining adequate sensitivity while operating under stringency conditions required to accommodate highly complex samples.

An array is "addressable" when it has multiple regions of different moieties, i.e., features (e.g.,each made up of different oligonucleotide sequences) such that a region (i.e., a "feature" or "spot" of the array) at a particular predetermined location (i.e., an "address") on the array will detect a particular solution phase nucleic acid sequence. Array features are typically, but need not be, separated by intervening spaces.

Figure 2:
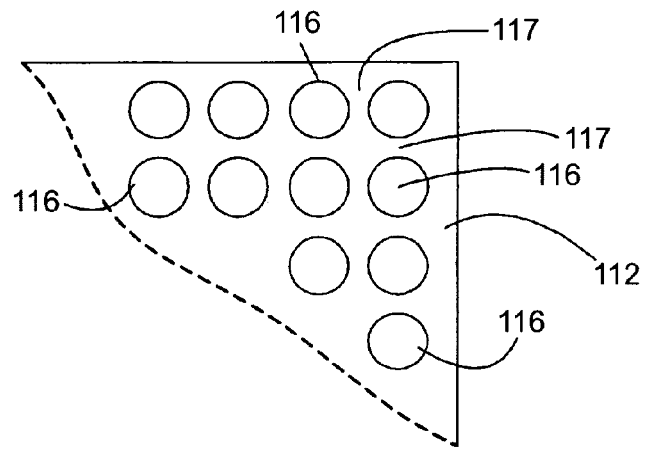
FIG. 2 shows an enlarged view of a portion of FIG. 1 showing spots or features.
Figure 3:
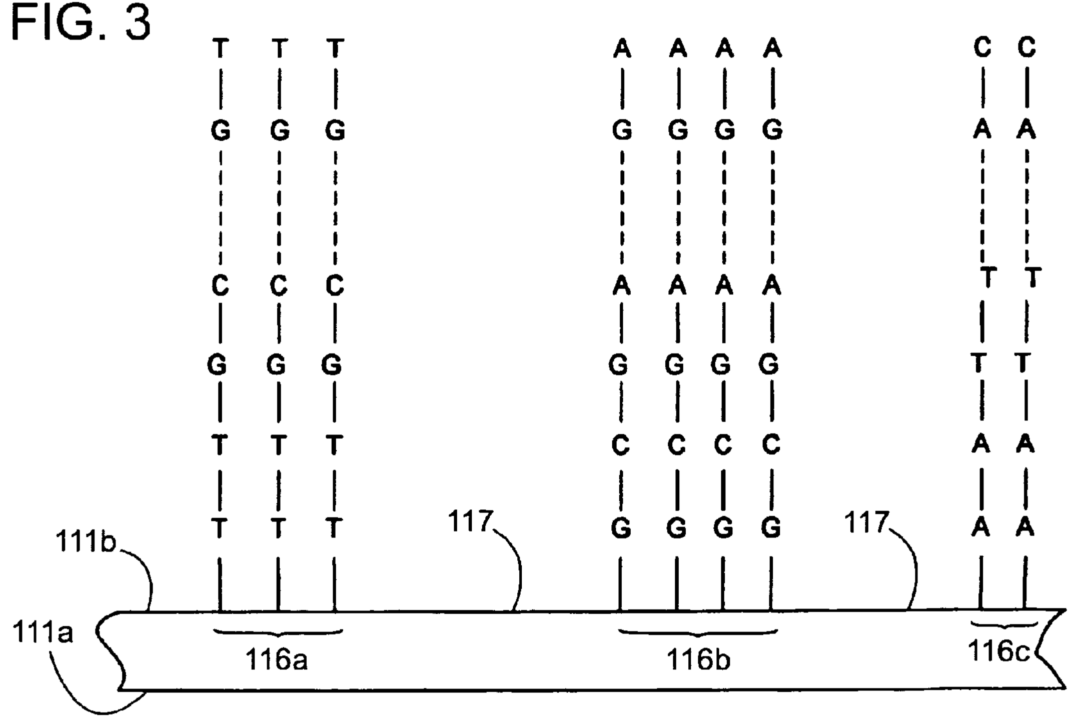
FIG. 3 is an enlarged view of a portion of the substrate of FIG. 1.

An exemplary array is shown in FIGS. 1-3, where the array shown in this representative embodiment includes a contiguous planar substrate 110 carrying an array 112 disposed on a rear surface 111*b* of substrate 110. It will be appreciated though, that more than one array (any of which are the same or different) may be present on rear surface 111*b*, with or without spacing between such arrays. That is, any given substrate may carry one, two, four or more arrays disposed on a front surface of the substrate and depending on the use of the array, any or all of the arrays may be the same or different from one another and each may contain multiple spots or features. The one or more arrays 112 usually cover only a portion of the rear surface 111*b*, with regions of the rear surface 111*b* adjacent the opposed sides 113*c*, 113*d* and leading end 113*a* and trailing end 113*b* of slide 110, not being covered by any array 112. A front surface 111*a* of the slide 110 does not carry any arrays 112. Each array 112 can be designed for testing against any type of sample, whether a trial sample, reference sample, a combination of them, or a known mixture of biopolymers such as polynucleotides. Substrate 110 may be of any shape, as mentioned above.

As mentioned above, array 112 contains multiple spots or features 116 of oligomers, e.g., in the form of polynucleotides, and specifically oligonucleotides. As mentioned above, all of the features 116 may be different, or some or all could be the same. The interfeature areas 117 could be of various sizes and configurations. Each feature carries a predetermined oligomer such as a predetermined polynucleotide (which includes the possibility of mixtures of polynucleotides). It will be understood that there may be a linker molecule (not shown) of any known types between the rear surface 111*b* and the first nucleotide.

Substrate 110 may carry on front surface 111*a*, an identification code, e.g., in the form of bar code (not shown) or the like printed on a substrate in the form of a paper label attached by adhesive or any convenient means. The identification code contains information relating to array 112, where such information may include, but is not limited to, an identification of array 112, i.e., layout information relating to the array(s), etc.

In the case of an array in the context of the present application, the "target" may be referenced as a moiety in a mobile phase (typically fluid), to be detected by "probes" which are bound to the substrate at the various regions.

A "scan region" refers to a contiguous (preferably, rectangular) area in which the array spots or features of interest, as defined above, are found or detected. Where fluorescent labels are employed, the scan region is that portion of the total area illuminated from which the resulting fluorescence is detected and recorded. Where other detection protocols are employed, the scan region is that portion of the total area queried from which resulting signal is detected and recorded. For the purposes of this invention and with respect to fluorescent detection embodiments, the scan region includes the entire area of the slide scanned in each pass of the lens, between the first feature of interest, and the last feature of interest, even if there exist intervening areas that lack features of interest.

An "array layout" refers to one or more characteristics of the features, such as feature positioning on the substrate, one or more feature dimensions, and an indication of a moiety at a given location. "Hybridizing" and "binding", with respect to nucleic acids, are used interchangeably.

By "remote location," it is meant a location other than the location at which the array is present and hybridization occurs. For example, a remote location could be another location (e.g., office, lab, etc.) in the same city, another location in a different city, another location in a different state, another location in a different country, etc. As such, when one item is indicated as being "remote" from another, what is meant is that the two items are at least in different rooms or different buildings, and may be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise is (where that is possible) and includes, at least in the case of data, physically transporting a medium carrying the data or communicating the data. An array "package" may be the array plus only a substrate on which the array is deposited, although the package may include other features (such as a housing with a chamber). A "chamber" references an enclosed volume (although a chamber may be accessible through one or more ports). It will also be appreciated that throughout the present application, that words such as "top," "upper," and "lower" are used in a relative sense only.

The term "stringent assay conditions" as used herein refers to conditions that are compatible to produce binding pairs of nucleic acids, e.g., surface bound and solution phase nucleic acids, of sufficient complementarity to provide for the desired level of specificity in the assay while being less compatible to the formation of binding pairs between binding members of insufficient complementarity to provide for the desired specificity. Stringent assay conditions are the summation or combination (totality) of both hybridization and wash conditions.

A "stringent hybridization" and "stringent hybridization wash conditions" in the context of nucleic acid hybridization (e.g., as in array, Southern or Northern hybridizations) are sequence dependent, and are different under different experimental parameters. Stringent hybridization conditions that can be used to identify nucleic acids within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1 M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions that set forth the conditions which determine whether a nucleic acid is specifically hybridized to a surface bound nucleic acid. Wash conditions used to identify nucleic acids may include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be, e.g., 0.2×SSC/0.1% SDS at 42° C.

A specific example of stringent assay conditions is rotating hybridization at 65° C. in a salt based hybridization buffer with a total monovalent cation concentration of 1.5 M (e.g., as described in U.S. patent application Ser. No. 09/655,482 filed on Sep. 5, 2000, the disclosure of which is herein incorporated by reference) followed by washes of 0.5×SSC and 0.1×SSC at room temperature.

Stringent assay conditions are hybridization conditions that are at least as stringent as the above representative conditions, where a given set of conditions are considered to be at least as stringent if substantially no additional binding complexes that lack sufficient complementarity to provide for the desired specificity are produced in the given set of conditions as compared to the above specific conditions, where by "substantially no more" is meant less than about 5-fold more, typically less than about 3-fold more. Other stringent hybridization conditions are known in the art and may also be employed, as appropriate.

Sensitivity is a term used to refer to the ability of a given assay to detect a given analyte in a sample, e.g., a nucleic acid species of interest. For example, an assay has high sensitivity if it can detect a small concentration of analyte molecules in sample. Conversely, a given assay has low sensitivity if it only detects a large concentration of analyte molecules (i.e., specific solution phase nucleic acids of interest) in sample. A given assay's sensitivity is dependent on a number of parameters, including specificity of the reagents employed (e.g., types of labels, types of binding molecules, etc.), assay conditions employed, detection protocols employed, and the like. In the context of array hybridization assays, such as those of the present invention, sensitivity of a given assay may be dependent upon one or more of: the nature of the surface immobilized nucleic acids, the nature of the hybridization and wash conditions, the nature of the labeling system, the nature of the detection system, etc.

DESCRIPTION OF THE SPECIFIC EMBODIMENTS

Comparative genomic hybridization assays and compositions for use in practicing the same are provided. A characteristic of the subject comparative genomic hybridization assays is that solid support immobilized oligonucleotide features, e.g., in the form of an array, are employed. Specifically, at least first and second nucleic acid populations prepared from genomic sources are contacted with a plurality of distinct oligonucleotide features immobilized on a solid support surface and the binding of the at least first and second populations is then evaluated. Also provided are kits for use in practicing the subject methods.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the invention components that are described in the publications that might be used in connection with the presently described invention.

As summarized above, the present invention provides methods for comparing populations of nucleic acids, e.g., in array Comparative Genomic Hybridization (aCGH) applications, and compositions for use therein. In further describing the present invention, the subject methods are discussed first in greater detail, followed by a review of representative kits for use in practicing the subject methods.

Methods

The subject invention provides methods for comparing populations of nucleic acids and compositions for use therein, where a characteristic of the subject methods is the use of a population of distinct substrate immobilized oligonucleotide features, e.g., an array of substrate immobilized oligonucleotide features.

In practicing the subject methods, the first step is to provide at least two different populations or collections of nucleic acids that are to be compared. The two or more populations of nucleic acids may or may not be labeled, depending on the particular detection protocol employed in a given assay. For example, in certain embodiments, binding events on the surface of a substrate may be detected by means other than by detection of a labeled nucleic acids, such as by change in conformation of a conformationally labeled immobilized oligonucleotide, detection of electrical signals caused by binding events on the substrate surface, etc. In many embodiments, however, the populations of nucleic acids are labeled, where the populations may be labeled with the same label or different labels, depending on the actual assay protocol employed. For example, where each population is to be contacted with different but identical arrays, each nucleic acid population or collection may be labeled with the same label. Alternatively, where both populations are to be simultaneously contacted with a single array of immobilized oligonucleotide features, i.e., cohybridized to the same array of immobilized nucleic acid feature, solution-phase collections or populations of nucleic acids that are to be compared are generally distinguishably or differentially labeled with respect to each other.

The two or more (i.e., at least first and second, where the number of different collections may, in certain embodiments, be three, four or more) populations of nucleic acids are prepared from different genomic sources. As such, the first step in many embodiments of the subject methods is to prepare a collection of nucleic acids, e.g., labeled nucleic acids, from an initial genomic source for each genome that is to be compared.

The term genome refers to all nucleic acid sequences (coding and non-coding) and elements present in or originating from any virus, single cell (prokaryote and eukaryote) or each cell type and their organelles (e.g. mitochondria) in a metazoan organism. The term genome also applies to any naturally occurring or induced variation of these sequences that may be present in a mutant or disease variant of any virus or cell type. These sequences include, but are not limited to, those involved in the maintenance, replication, segregation, and higher order structures (e.g. folding and compaction of DNA in chromatin and chromosomes), or other functions, if any, of the nucleic acids as well as all the coding regions and their corresponding regulatory elements needed to produce and maintain each particle, cell or cell type in a given organism.

For example, the human genome consists of approximately $3\times10^9$ base pairs of DNA organized into distinct chromosomes. The genome of a normal diploid somatic human cell consists of 22 pairs of autosomes (chromosomes 1 to 22) and either chromosomes X and Y (males) or a pair of chromosome Xs (female) for a total of 46 chromosomes. A genome of a cancer cell may contain variable numbers of each chromosome in addition to deletions, rearrangements and amplification of any subchromosomal region or DNA sequence.

By "genomic source" is meant the initial nucleic acids that are used as the original nucleic acid source from which the solution phase nucleic acids are produced, e.g., as a template in the labeled solution phase nucleic acid generation protocols described in greater detail below.

The genomic source may be prepared using any convenient protocol. In many embodiments, the genomic source is prepared by first obtaining a starting composition of genomic DNA, e.g., a nuclear fraction of a cell lysate, where any convenient means for obtaining such a fraction may be employed and numerous protocols for doing so are well known in the art. The genomic source is, in many embodiments of interest, genomic DNA representing the entire genome from a particular organism, tissue or cell type. However, in certain embodiments the genomic source may comprise a portion of the genome, e.g., one or more specific chromosomes or regions thereof, such as PCR amplified regions produced with a pairs of specific primers.

A given initial genomic source may be prepared from a subject, for example a plant or an animal, which subject is suspected of being homozygous or heterozygous for a deletion or amplification of a genomic region. In certain embodiments, the average size of the constituent molecules that make up the initial genomic source typically have an average size of at least about 1 Mb, where a representative range of sizes is from about 50 to about 250 Mb or more, while in other embodiments, the sizes may not exceed 20 about 1 MB, such that they may be about 1 Mb or smaller, e.g., less than about 500 Kb, etc.

In certain embodiments, the genomic source is "mammalian", where this term is used broadly to describe organisms which are within the class mammalia, including the orders carnivore (e.g., dogs and cats), rodentia (e.g., mice, guinea pigs, and rats), and primates (e.g., humans, chimpanzees, and monkeys), where of particular interest in certain embodiments are human or mouse genomic sources. In certain embodiments, a set of nucleic acid sequences within the genomic source is complex, as the genome containsat least about $1\times10^8$ base pairs, including at least about $1\times10^9$ base pairs, e.g., about $3\times10^9$ base pairs.

Where desired, the initial genomic source may be fragmented in the generation protocol, as desired, to produce a fragmented genomic source, where the molecules have a desired average size range, e.g., up to about 10 Kb, such as up to about 1 Kb, where fragmentation may be achieved using any convenient protocol, including but not limited to: mechanical protocols, e.g., sonication, shearing, etc., chemical protocols, e.g., enzyme digestion, etc.

Where desired, the initial genomic source may be amplified as part of the solution phase nucleic acid generation protocol, where the amplification may or may not occur prior to any fragmentation step. In those embodiments where the produced collection of nucleic acids has substantially the same complexity as the initial genomic source from which it is prepared, the amplification step employed is one that does not reduce the complexity, e.g., one that employs a set of random primers, as described below. For example, the initial genomic source may first be amplified in a manner that results in an amplified version of virtually the whole genome, if not the whole genome, before labeling, where the fragmentation, if employed, may be performed pre- or post-amplification.

Following provision of the initial genomic source, and any initial processing steps (e.g., fragmentation, amplification, etc.) as described above, the collection of solution phase nucleic acids is prepared for use in the subject methods. In certain embodiments of particular interest, the collection of solution phase nucleic acids prepared from the initial genomic source is one that has substantially the same complexity as the complexity of the initial genomic source. Complexity, as used in describing the product nucleic acid collection/population, refers to the number of distinct or different nucleic acid sequences found in a collection of nucleic acids relative to the number of distinct or different nucleic acid sequences found in the genomic source.

The prepared collection of solution phase nucleic acids is a "non-reduced-complexity" collection of solution phase nucleic acids as compared to the initial genomic source. A non-reduced complexity collection is one that is not produced in a manner designed to reduce the complexity of the sample. Examples of protocols that can produce reduced complexity product compositions of utility in genotyping and gene expression include those described in U.S. Pat. No. 6,465,182 and published PCT application WO 99/23256; as well as published U.S. patent application Ser. No. 2003/0036069 and Jordan et al., Proc. Nat'l Acad. Sci. USA (Mar. 5, 2002) 99: 2942-2947. In each of these protocols that produce a reduced complexity product, primers are employed that have been designed to knowingly produce product nucleic acids from only a select fraction or portion of the initial genomic source, e.g., genome, where fraction or portion may be defined as a subset or representative subset of a genome.

A product composition is considered to be a non-reduced complexity product composition as compared to the initial nucleic acid source from which it is prepared if there is a high probability that a sequence of specific length randomly chosen from the sequence of the initial genomic source is present in the product composition, either in a single nucleic acid member of the product or in a "concatamer" of two different nucleic acid members of the product (i.e., in a virtual molecule produced by joining two different members to produce a single molecule). In other words, if there is a high probably that an N-mer sequence (i.e., a sequence of "N" nucleotides) that is randomly chosen from the initial source has the same sequence as an N-mer within the product composition (either in a single nucleic acid member of the product or in a "concatamer" of two different nucleic acid members of the product), then the product composition is considered to be a composition of non-reduced complexity as compared to the initial source. In many embodiments, the length N of the sequence (i.e., N-mer) that is randomly chosen from the initial source ranges from about 45 to about 200 nt, including from about 50 to about 100 nt, such as from about 55 to about 65 nt, e.g., 60 nt. For example, if a sequence of 60 nt in length that is randomly chosen uniformly over an initial genomic source sequence has a high probability of being in the product composition, then the product composition has a non-reduced complexity as compared to the parent composition. For this purpose, a given sequence is considered to have a high probability of being in a product composition if its probability of being in the product composition, either in a single nucleic acid member or in a concatamer of two different members, is at least about 10%, for example at least about 25%, including at least about 50%, where in certain embodiments the probability may be about 60%, about 70%, about 80%, about 90%, about 95% or higher, e.g., about 98%, etc. With knowledge of the sequence within the genomic source and product, the probability that a given sequence randomly chosen from the initial source is present in a given product composition may be determined according to the following parameters:

Consider a nucleotide sequence of the genomic source: G. Consider a fixed integer N. Consider a collection of nucleic acids, $M=\{m_1, m_2, \ldots, m_k\}$ where each $m_i$ is a subsequence of G. For any N-mer sequence w, define $$\sigma_G(w) = \begin{cases} 1 & w \text{ is a subsequence of } G \\ 0 & \text{otherwise} \end{cases}$$

$$\sigma_M(w) = \begin{cases} 1 & w \text{ is a subsequence of some } m_i \\ & \text{or of some concatenation } m_i * m_j \\ 0 & \text{otherwise} \end{cases}$$

Set $$S_G = \sum_{N\text{-}mers} \sigma_G(w)$$

and $$S_M = \sum_{N\text{-}mers} \sigma_M(w)$$

Where the sums are over all mathematically possible N-mers. The probability that a random N-mer W uniformly selected over G is present in M is then $$p = \frac{S_M}{S_G}.$$

From a practical point of view, the numbers $S_M$ and $S_G$ can be computed by stepping along the sequences and incrementing by 1 every time a new N-mer is visited. Then all pairs of concatemers from M are also processed in the same way. Given the formulas, this calculation is then obvious to anyone skilled in the art of programming.

A non-reduced complexity collection of nucleic acids can be readily identified using a number of different protocols. One convenient protocol for determining whether a given collection of nucleic acids is a non-reduced complexity collection of nucleic acids is to screen the collection using a genome wide array of features for the initial, e.g., genomic source of interest. Thus, one can tell whether a given collection of nucleic acids has non-reduced complexity with respect to its genomic source by assaying the collection with a genome wide array for the genomic source. The genome wide array of the genomic source for this purpose is an array of features in which the collection of features of the array used to test the sample is made up of sequences uniformly and independently randomly chosen from the initial genomic source. As such, sequences of sufficient length, e.g., N length as described above, independently chosen randomly from the initial nucleic acid source that uniformly sample the initial nucleic acid source are present in the collection of features on the array. By uniformly is meant that no bias is present in the selection of sequences from the initial genomic source. In such a genome wide assay of sample, a non-reduced complexity sample is one in which substantially all of the array features on the array specifically hybridize to nucleic acids present in the sample, where by substantially all is meant at least about 10%, for example at least about 25%, including at least about 50%, such as at least about 60, 70, 75, 80, 85, 90 or 95% or more.

As such, according to the above guidelines, a sample is considered to be of non-reduced complexity as compared to its genomic source if its complexity is at least about 10%, for example at least about 25%, including at least about 50%, such as at least about 60, 70, 75, 80, 85, 90 or 95% or more of the complexity of the genomic source, as detailed above.

In many embodiments of interest, the collection or population of nucleic acids that is prepared in this step of the subject methods is one that is labeled with a detectable label.

In the embodiments where the population of solution-phase nucleic acids is a non-reduced complexity population of nucleic acids, as described above, the labeled nucleic acids are prepared in a manner that does not reduce the complexity to any significant extent as compared to the initial genomic source. A number of different nucleic acid labeling protocols are known in the art and may be employed to produce a population of labeled nucleic acids. The particular protocol may include the use of labeled primers, labeled nucleotides, modified nucleotides that can be conjugated with different dyes, one or more amplification steps, etc.

In one type of representative labeling protocol of interest, the initial genomic source, which most often is fragmented (as described above), is employed in the preparation of labeled nucleic acids as a genomic template from which the labeled nucleic acids are enzymatically produced. Different types of template dependent labeled nucleic acid generation protocols are known in the art. In certain types of protocols, the template is employed in a non-amplifying primer extension nucleic acid generation protocol. In yet other embodiments, the template is employed in an amplifying primer extension protocol.

Of interest in the embodiments described above, whether they be amplifying or non-amplifying primer extension reactions, is the use of a set of primers that results in the production of the desired nucleic acid collection of high complexity, i.e., comparable or substantially similar complexity to the initial genomic source. In many embodiments, the above described population of nucleic acids in which substantially all, if not all, of the sequences found in the initial genomic source are present, is produced using a primer mixture of random primers, i.e., primers of random sequence. The primers employed in the subject methods may vary in length, and in many embodiments range in length from about 3 to about 25 nt, sometimes from about 5 to about 20 nt and sometimes from about 5 to about 10 nt. The total number of random primers of different sequence that is present in a given population of random primers may vary, and depends on the length of the primers in the set. As such, in the sets of random primers, which include all possible variations, the total number of primers n in the set of primers that is employed is $4^Y$, where Y is the length of the primers. Thus, where the primer set is made up of 3-mers, Y=3 and the total number n of random primers in the set is $4^3$ or 64. Likewise, where the primer set is made up of 8-mers, Y=8 and the total number n of random primers in the set is $4^8$ or 65,536. Typically, an excess of random primers is employed, such that in a given primer set employed in the subject invention, multiple copies of each different random primer sequence is present, and the total number of primer molecules in the set far exceeds the total number of distinct primer sequences, where the total number may range from about $1.0\times10^{10}$ to about $1.0\times10^{20}$, such as from about $1.0\times10^{13}$ to about $1.0\times10^{17}$, e.g., $3.7\times10^{15}$. The primers described above and throughout this specification may be prepared using any suitable method, such as, for example, the known phosphotriester and phosphite triester methods, or automated embodiments thereof. In one such automated embodiment, dialkyl phosphoramidites are used as starting materials and may be synthesized as described by Beaucage et aL. (1981), Tetrahedron Letters 22, 1859. One method for synthesizing oligonucleotides on a modified solid support is described in U.S. Pat. No. 4,458,066.

As indicated above, in generating labeled nucleic acids according to these embodiments of subject methods, the above-described genomic template and random primer population are employed together in a primer extension reaction that produces the desired labeled nucleic acids. Primer extension reactions for generating labeled nucleic acids are well known to those of skill in the art, and any convenient protocol may be employed, so long as the above described genomic source (being used as a template) and population of random primers are employed. In this step of the subject methods, the primer is contacted with the template under conditions sufficient to extend the primer and produce a primer extension product, either in an amplifying or in a non-amplifying manner (where a non-amplifying manner is one in which essentially a single product is produced per template strand). As such, the above primers are contacted with the genomic template in the presence of a sufficient DNA polymerase under primer extension conditions sufficient to produce the desired primer extension molecules. DNA polymerases of interest include, but are not limited to, polymerases derived from *E. coli*, thermophilic bacteria, archaebacteria, phage, yeasts, Neurosporas, Drosophilas, primates and rodents. The DNA polymerase extends the primer according to the genomic template to which it is hybridized in the presence of additional reagents which may include, but are not limited to: dNTPs; monovalent and divalent cations, e.g. KCl, $MgCl_2$; sulfhydryl reagents, e.g. dithiothreitol; and buffering agents, e.g. Tris-Cl.

Extension products that are produced as described above are typically labeled in the present methods. As such, the reagents employed in the subject primer extension reactions typically include a labeling reagent, where the labeling reagent may be the primer or a labeled nucleotide, which may be labeled with a directly or indirectly detectable label. A directly detectable label is one that can be directly detected without the use of additional reagents, while an indirectly detectable label is one that is detectable by employing one or more additional reagent, e.g., where the label is a member of a signal producing system made up of two or more components. In many embodiments, the label is a directly detectable label, such as a fluorescent label, where the labeling reagent employed in such embodiments is a fluorescently tagged nucleotide(s), e.g., dCTP. Fluorescent moieties which may be used to tag nucleotides for producing labeled nucleic acids include, but are not limited to: fluorescein, the cyanine dyes, such as Cy3, Cy5, Alexa 555, Bodipy 630/650, and the like. Other labels may also be employed as are known in the art.

In the primer extension reactions employed in the subject methods of these embodiments, the genomic template is typically first subjected to strand disassociation conditions, e.g., subjected to a temperature ranging from about 80° C. to about 100° C., usually from about 90° C. to about 95° C. for a period of time, and the resultant disassociated template molecules are then contacted with the primer molecules under annealing conditions, where the temperature of the template and primer composition is reduced to an annealing temperature of from about 20° C. to about 80° C., usually from about 37° C. to about 65° C. In certain embodiments, a "snap-cooling" protocol is employed, where the temperature is reduced to the annealing temperature, or to about 4° C. or below in a period of from about 1 s to about 30s, usually from about 5s to about 10s.

The resultant annealed primer/template hybrids are then maintained in a reaction mixture that includes the above-discussed reagents at a sufficient temperature and for a sufficient period of time to produce the desired labeled nucleic acids. Typically, this incubation temperature ranges from about 20° C. to about 75° C., usually from about 37° C. to about 65° C. The incubation time typically ranges from about 5 min to about 18 hr, usually from about 1 hr to about 12 hr.

Using the above protocols, at least a first collection of nucleic acids and a second collection of nucleic acids are produced from two different genomic sources, e.g., a reference and test genomic template. As indicated above, depending on the particular assay protocol (e.g., whether both populations are to be hybridized simultaneously to a single array or whether each population is to be hybridized to two different but substantially identical, if not identical, arrays) the populations may be labeled with the same or different labels. As such, a characteristic of certain embodiments is that the different collections or populations of produced labeled nucleic acids are all labeled with the same label, such that they are not distinguishably labeled. In yet other embodiments, a characteristic of the different collections or populations of produced labeled nucleic acids is that the first and second labels are typically distinguishable from each other. The constituent members of the above produced collections typically range in length from about 100 to about 10,000 nt, such as from about 200 to about 10,000 nt, including from about 100 to 1,000 nt, from about 100 to about 500 nt, etc.

In the next step of the subject methods, the collections or populations of labeled nucleic acids produced by the subject methods are contacted to a plurality of different surface immobilized elements (i.e., features) under conditions such that nucleic acid hybridization to the surface immobilized elements can occur. The collections can be contacted to the surface immobilized elements either simultaneously or serially. In many embodiments the compositions are contacted with the plurality of surface immobilized elements, e.g., the array of distinct oligonucleotides of different sequence, simultaneously. Depending on how the collections or populations are labeled, the collections or populations may be contacted with the same array or different arrays, where when the collections or populations are contacted with different arrays, the different arrays are substantially, if not completely, identical to each other in terms of feature content and organization.

A characteristic of the present invention is that the substrate immobilized nucleic acids that make up the features of the arrays employed in the subject methods are oligonucleotides. By oligonucleotide is meant a nucleic acid having a length ranging from about 10 to about 200 nt including from about 10 or about 20 nt to about 100 nt, where in many embodiments the immobilized nucleic acids range in length from about 50 to about 90 nt or about 50 to about 80 nt, such as from about 50 to about 70 nt.

Surface immmobilized nucleic acids that make up the features of the arrays employed in such applications can be derived from virtually any source. Typically, the nucleic acids will be nucleic acid molecules having sequences derived from representative locations along a chromosome of interest, a chromosomal region of interest, an entire genome of interest, a cDNA library, and the like.

The choice of surface immobilized nucleic acids to use may be influenced by prior knowledge of the association of a particular chromosome or chromosomal region with certain disease conditions. International Application WO 93/18186 provides a list of chromosomal abnormalities and associated diseases, which are described in the scientific literature. Alternatively, whole genome screening to identify new regions subject to frequent changes in copy number can be performed using the methods of the present invention. In these embodiments, surface immobilized elements or features usually contain nucleic acids representative of locations distributed over the entire genome. In such embodiments, the resolution may vary, where in certain embodiments, the resolution is at least about 500 kb, such as at least about 250 kb, at least about 200 kb, at least about 150 kb, at least about 100 kb, at least about 50 kb, including at least about 25 kb, at least about 10 kb or higher. Of interest in certain embodiments are resolutions ranging from about 20 kb to about 100 kb, such as 30 kb to about 100 kb, including from about 40 kb to about 75 kb. By resolution is meant the spacing on the genome between sequences found in the surface immobilized elements or features. In some embodiments (e.g., using a large number of features of high complexity) all sequences in the genome can be present in the array. In certain embodiments, the resolution is with respect to at least a portion of the genmome, and may be about every 1 kb, about every 2 kb, about every 5 kb, about every 10 kb, as well as the numbers provided above. The spacing between different locations of the genome that are represented in the features of the collection of features may also vary, and may be uniform, such that the spacing is substantially the same, if not the same, between sampled regions, or non-uniform, as desired.

In some embodiments, previously identified regions from a particular chromosomal region of interest are used as array elements. Such regions are becoming available as a result of rapid progress of the worldwide initiative in genomics. In certain embodiments, the array can include features made up of surface immobilized oligonucleotides which “tile” a particular region (which have been identified in a previous assay), by which is meant that the features correspond to region of interest as well as genomic sequences found at defined intervals on either side of the particular region of interest, i.e., 5' and 3' of, the region of interest, where the intervals may or may not be uniform, and may be tailored with respect to the particular region of interest and the assay objective. In other words, the tiling density may be tailored based on the particular region of interest and the assay objective. Such “tiled” arrays and assays employing the same are useful in a number of applications, including applications where one identifies a region of interest at a first resolution, and then uses tiled arrays tailored to the initially identified region to further assay the region at a higher resolution, e.g., in an iterative protocol. Accordingly, the subject methods include at least two iterations, where the first iteration of the subject methods identifies a region of interest, and the one or more subsequent iterations assay the region with sets of tiled surface immobilized features, e.g., of increasing or alternate resolution.

Of interest are both coding and non-coding genomic regions, (as well as regions that are transcribed but not translated), where by coding region is meant a region of one or more exons that is transcribed into an mRNA product and from there translated into a protein product, while by non-coding region is meant any sequences outside of the exon regions, where such regions may include regulatory sequences, e.g., promoters, enhancers, introns, inter-genic regions, etc. In certain embodiments, one can have at least some of the features directed to non-coding regions and others directed to coding regions. In certain embodiments, one can have all of the features directed to non-coding sequences. In certain embodiments, one can have all of the features directed to, i.e., corresponding to, coding sequences.

In certain embodiments, the oligonucleotides that make up the distinct features are ones that have been designed according to one or more particular parameters to be suitable for use in a given application, where representative parameters include, but are not limited to: length, melting temperature (TM), non-homology with other regions of the genome, signal intensities, kinetic properties under hybridization conditions, etc., see e.g., U.S. Pat. No. 6,251,588, the dislcosure of which is herein incorporated by reference. In certain embodiments, the entire length of the feature oligonucleotides is employed in hybridizing to sequences in the genome, while in other embodiments, only a portion of the immobilized oligonucleotide has sequence that hybridizes to sequence found in the genome of interest, e.g., where a portion of the oligonucleotide serves as a tether. For example, a given oligonucleotide may include a 30 nt long genome specific sequence linked to a 30 nt tether, such that the oligonucleotide is a 60-mer of which only a portion, e.g., 30 nt long, is genome specific.

The surface immobilized oligonucleotides of the features employed in the subject methods are immobilized on a solid support. Many methods for immobilizing nucleic acids on a variety of solid support surfaces are known in the art. For instance, the solid support may be a membrane, glass, plastic, or a bead. The desired component may be covalently bound or noncovalently attached through nonspecific binding, adsorption, physisorption or chemisorption. The immobilization of nucleic acids on solid support surfaces is discussed more fully below.

A wide variety of organic and inorganic polymers, as well as other materials, both natural and synthetic, may be employed as the material for the solid surface. Illustrative solid surfaces include nitrocellulose, nylon, glass, fused silica, diazotized membranes (paper or nylon), silicones, cellulose, and cellulose acetate. In addition, plastics such as polyethylene, polypropylene, polystyrene, and the like can be used. Other materials that may be employed include paper, ceramics, metals, metalloids, semiconductive materials, cermets or the like. In addition substances that form gels can be used. Such materials include proteins (e.g., gelatins), lipopolysaccharides, silicates, agarose and polyacrylamides. Where the solid surface is porous, various pore sizes may be employed depending upon the nature of the system.

As reviewed above, arrays can be fabricated using a variety of different protocols. Of interest in certain embodiments are arrays prepared by drop deposition from pulse-jets of either nucleic acid precursor units (such as monomers) in the case of in situ fabrication, or the previously obtained nucleic acid. Such methods are described in detail in, for example, the previously cited references including U.S. Pat. Nos. 6,242,266, 6,232,072, 6,180,351, 6,171,797, 6,323,043, U.S. patent application Ser. No. 09/302,898 filed Apr. 30, 1999 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used. Inter-feature areas need not be present, particularly when the arrays are made by photolithographic methods as described in those patents. Of particular interest in certain embodiments are arrays produced via in situ preparation protocols.

In the subject methods (as summarized above), the copy number of particular nucleic acid sequences in two solution phase collections are compared by hybridizing the collections to one or more nucleic acid, specifically oligonucleotide, arrays, as described above. The hybridization signal intensity, and the ratio of intensities, read from any resultant surface immobilized nucleic acid duplexes (made up of hybridized feature oligonucleotides and solution phase nucleic acids) produced is determined. Since signal intensities on a feature can be influenced by factors other than the copy number of a solution phase nucleic acid population, for certain embodiments an analysis is conducted where two labeled populations are present with distinct labels. Thus comparison of the signal intensities for a specific surface immobilized elements permits a direct comparison of copy number for a given sequence. Different surface immobilized elements will reflect the copy numbers for different sequences in the solution phase populations. The comparison can reveal situations where each sample includes a certain number of copies of a sequence of interest, but the numbers of copies in each sample are different. The comparison can also reveal situations where one sample is devoid of any copies of the sequence of interest, and the other sample includes one or more copies of the sequence of interest.

Standard hybridization techniques (using high stringency hybridization and washing conditions) are used to assay a nucleic acid array. Suitable methods are described in references describing CGH techniques (Kallioniemi et al., Science 258:818-821 (1992) and WO 93/18186). Several guides to general techniques are available, e.g., Tijssen, Hybridization with Nucleic Acid Probes, Parts I and II (Elsevier, Amsterdam 1993). For a descriptions of techniques suitable for in situ hybridizations see, Gall et al. Meth. Enzymol., 21:470480 (1981) and Angerer et al. in Genetic Engineering: Principles and Methods Setlow and Hollaender, Eds. Vol 7, pgs 43-65 (plenum Press, New York 1985). See also U.S. Pat. Nos. 6,335,167; 6,197,501; 5,830,645; and 5,665,549; the disclosures of which are herein incorporate by reference.

Generally, nucleic acid hybridizations comprise the-following major steps: (1) provision of array of surface immobilized nucleic acids or features; (2) optionally pre-hybridization treatment to increase accessibility of features, and to reduce nonspecific binding; (3) hybridization of the mixture of nucleic acids to the features on the solid surface, typically under high stringency conditions; (4) post-hybridization washes to remove nucleic acid fragments not bound in the hybridization; and (5) detection of the hybridized nucleic acid fragments. The reagents used in each of these steps and their conditions for use vary depending on the particular application.

As indicated above, hybridization is carried out under suitable hybridization conditions, which may vary in stringency as desired. In certain embodiments, highly stringent hybridization conditions may be employed. The term "highly stringent hybridization conditions" as used herein refers to conditions that are compatible to produce nucleic acid binding complexes on an array surface between complementary binding members, i.e., between immobilized features and complementary solution phase nucleic acids in a sample. Representative high stringency assay conditions that may be employed in these embodiments are provided above.

The above hybridization step may include agitation of the immobilized features and the sample of solution phase nucleic acids, where the agitation may be accomplished using any convenient protocol, e.g., shaking, rotating, spinning, and the like.

Following hybridization, the surface of immobilized nucleic acids is typically washed to remove unbound nucleic acids. Washing may be performed using any convenient washing protocol, where the washing conditions are typically stringent, as described above.

Following hybridization and washing, as described above, the hybridization of the labeled nucleic acids to the array is then detected using standard techniques so that the surface of immobilized features, e.g., array, is read. Reading of the resultant hybridized array may be accomplished by illuminating the array and reading the location and intensity of resulting fluorescence at each feature of the array to detect any binding complexes on the surface of the array. For example, a scanner may be used for this purpose which is similar to the AGILENT MICROARRAY SCANNER available from Agilent Technologies, Palo Alto, CA. Other suitable devices and methods are described in U.S. patent applications Ser. No. 09/846125 "Reading Multi-Featured Arrays" by Dorsel et al.; and U.S. Pat. No. 6,406,849, which references are incorporated herein by reference. However, arrays may be read by any other method or apparatus than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. No. 6,221,583 and elsewhere). In the case of indirect labeling, subsequent treatment of the array with the appropriate reagents may be employed to enable reading of the array. Some methods of detection, such as surface plasmon resonance, do not require any labeling of the nucleic acids, and are suitable for some embodiments.

Results from the reading or evaluating may be raw results (such as fluorescence intensity readings for each feature in one or more color channels) or may be processed results, such as obtained by subtracting a background measurement, or by rejecting a reading for a feature which is below a predetermined threshold and/or forming conclusions based on the pattern read from the array (such as whether or not a particular feature sequence may have been present in the sample, or whether or not a pattern indicates a particular condition of an organism from which the sample came).

In certain embodiments, the subject methods include a step of transmitting data or results from at least one of the detecting and deriving steps, also referred to herein as evaluating, as described above, to a remote location. By "remote location" is meant a location other than the location at which the array is present and hybridization occur. For example, a remote location could be another location (e.g. office, lab, etc.) in the same city, another location in a different city, another location in a different state, another location in a different country, etc. As such, when one item is indicated as being "remote" from another, what is meant is that the two items are at least in different buildings, and may be at least one mile, ten miles, or at least one hundred miles apart.

"Communicating" information means transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. The data may be transmitted to the remote location for further evaluation and/or use. Any convenient telecommunications means may be employed for transmitting the data, e.g., facsimile, modem, internet, etc.

A feature of the certain embodiments of the above methods is that they are sufficiently sensitive to detect a single copy number difference or change in the amount of a sequence of interest between any two given samples. In other words, the subject methods are capable of detecting a single copy number variation in a sequence between any two samples. As such, the subject methods are highly sensitive methods of comparing the copy numbers of one or more sequences between two or more samples.

Utility

The above-described methods find use in any application in which one wishes to compare the copy number of nucleic acid sequences found in two or more populations. One type of representative application in which the subject methods find use is the quantitative comparison of copy number of one nucleic acid sequence in a first collection of nucleic acid molecules relative to the copy number of the same sequence in a second collection. The subject methods find use in the detection of both heterozygous and homozygous deletions of sequences, as well as amplification of sequences, which conditions may be characteristic of certain conditions, e.g., disease conditions.

As such, embodiments of the present invention may be used in methods of comparing abnormal nucleic acid copy number and mapping of chromosomal abnormalities associated with disease. In certain embodiments, the subject methods are employed in applications that use nucleic acids immobilized on a solid support, to which differentially labeled solution phase nucleic acids produced as described above are hybridized. Analysis of processed results of the described hybridization experiments provides information about the relative copy number of nucleic acid domains, e.g. genes, in genomes.

Such applications compare the copy numbers of sequences capable of binding to the features. Variations in copy number detectable by the methods of the invention may arise in different ways. For example, copy number may be altered as a result of amplification or deletion of a chromosomal region, e.g. as commonly occurs in cancer.

Representative applications in which the subject methods find use are further described in U.S. Pat. Nos. 6,335,167; 6,197,501; 5,830,645; and 5,665,549; the disclosures of which are herein incorporated by reference.

Kits

Also provided are kits for use in the subject invention, where such kits may comprise containers, each with one or more of the various reagents/compositions utilized in the methods, where such reagents/compositions typically at least include a collection of immobilized oligonucleotide features, e.g., one or more arrays of oligonucleotide features, and reagents employed in labeled nucleic acid production, e.g., random primers, buffers, the appropriate nucleotide triphosphates (e.g. dATP, dCTP, dGTP, dTTP), DNA polymerase, labeling reagents, e.g., labeled nucleotides, and the like. Where the kits are specifically designed for use in CGH applications, the kits may further include labeling reagents for making two or more collections of distinguishably labeled nucleic acids according to the subject methods, an array of features, hybridization solution, etc.

Finally, the kits may further include instructions for using the kit components in the subject methods. The instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc.

The following examples are offered by way of illustration and not by way of limitation.

EXPERIMENTAL

I. Results and Discussion

Four different array types were used in these experiments. In the first set of experiments, male (XY) and female (XX) genomic DNA were prepared and hybridized to an Agilent Technologies 60 mer in situ synthesized oligonucleotide microarray (Array 1) according to the protocols described below in Materials and Methods. The arrays were prepared by the protocol described in U.S. Pat. No. 6,444,268 (the disclosure of which is herein incorporated by reference) with 60mer oligonucleotide sequences designed for the purposes of gene expression profiling studies for ~7.9K genes from the Ref Seq database of the NIH. (National Center for Biotechnology Information U.S. National Library of Medicine, 8600 Rockville Pike, Bethesda, Md. 20894)

The Cy5/Cy3 (XY/XX) ratios were calculated for features prepared from the X chromosome (273 features), Y chromosome (14 features) or all autosomes (7722 features). The average log2 ratio for autosomal features was 0.02 (+/−0.41) and for X chromosome features was −0.87 (+/−0.61). This result compares favorably to the expected ratios of 0.0 and −1.0 respectively. For the Y chromosome features present on the array, the expected ratios are undefined but should be greater than 1 because these sequences are present in the male XY DNA sample but absent in the female XX sample. Thus, the value in the denominator of the calculated ratio is very small and potentially near zero. An average log2 ratio for Y chromosome-specific sequences of 1.30 (+/−1.80) was observed.

The colon carcinoma cell line Colo320 contains a well-known amplification of the oncogene v-myc. Genomic DNA was isolated from this cell line and hybridized to Array 1 with normal female genomic reference DNA. The Cy5/Cy3 ratio for the v-myc nucleic acid indicated a 100-fold increase in this gene in the cell line over the normal reference. This result is within the range of v-myc amplification detected by other techniques in published studies (Nat. Genet. 2001, 29:263-264).

Figure 4A:
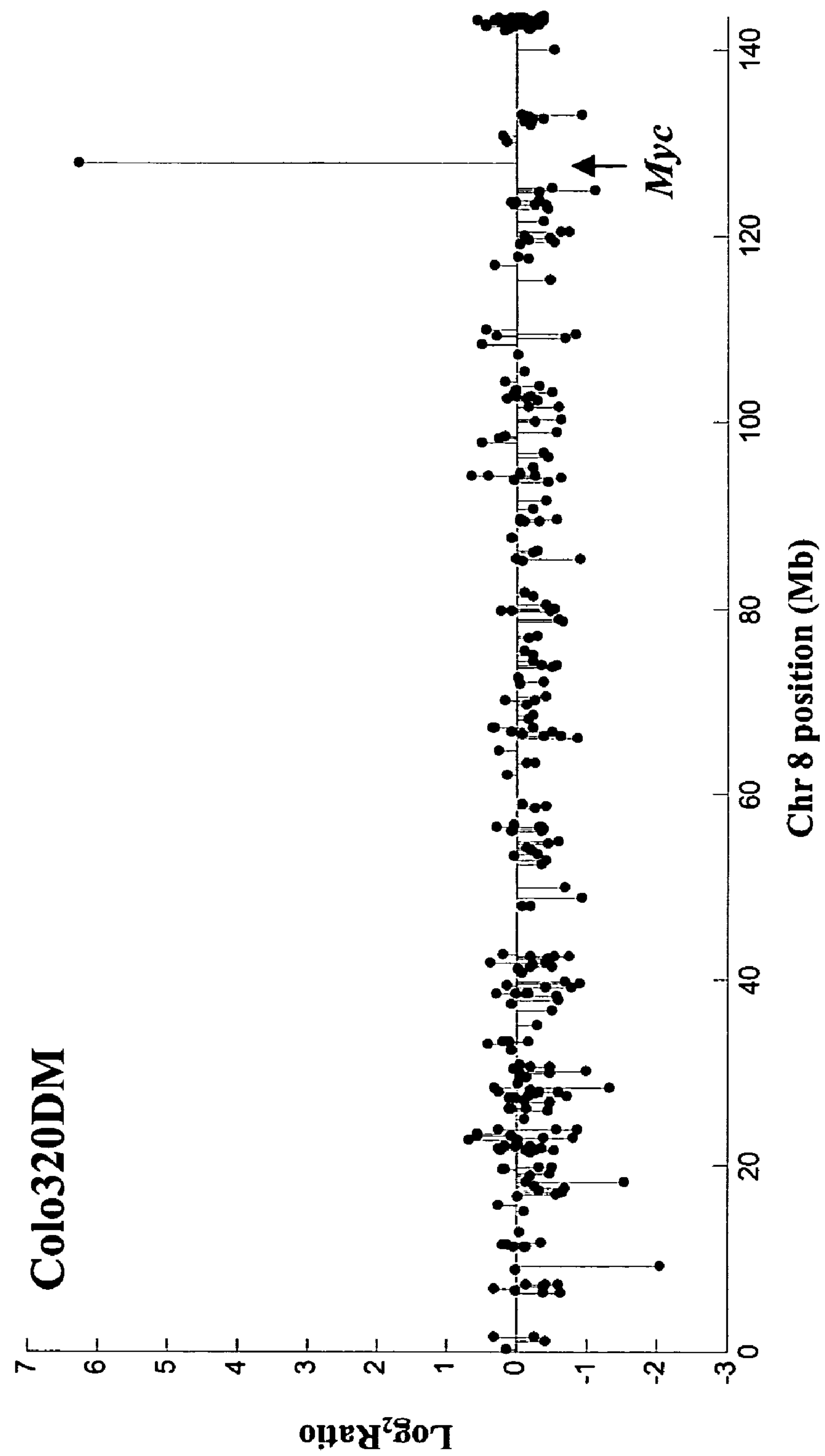
FIGS. 4 to 7 provide graphical results of various experiments reported in the Experimental section, below.
Figure 4B:
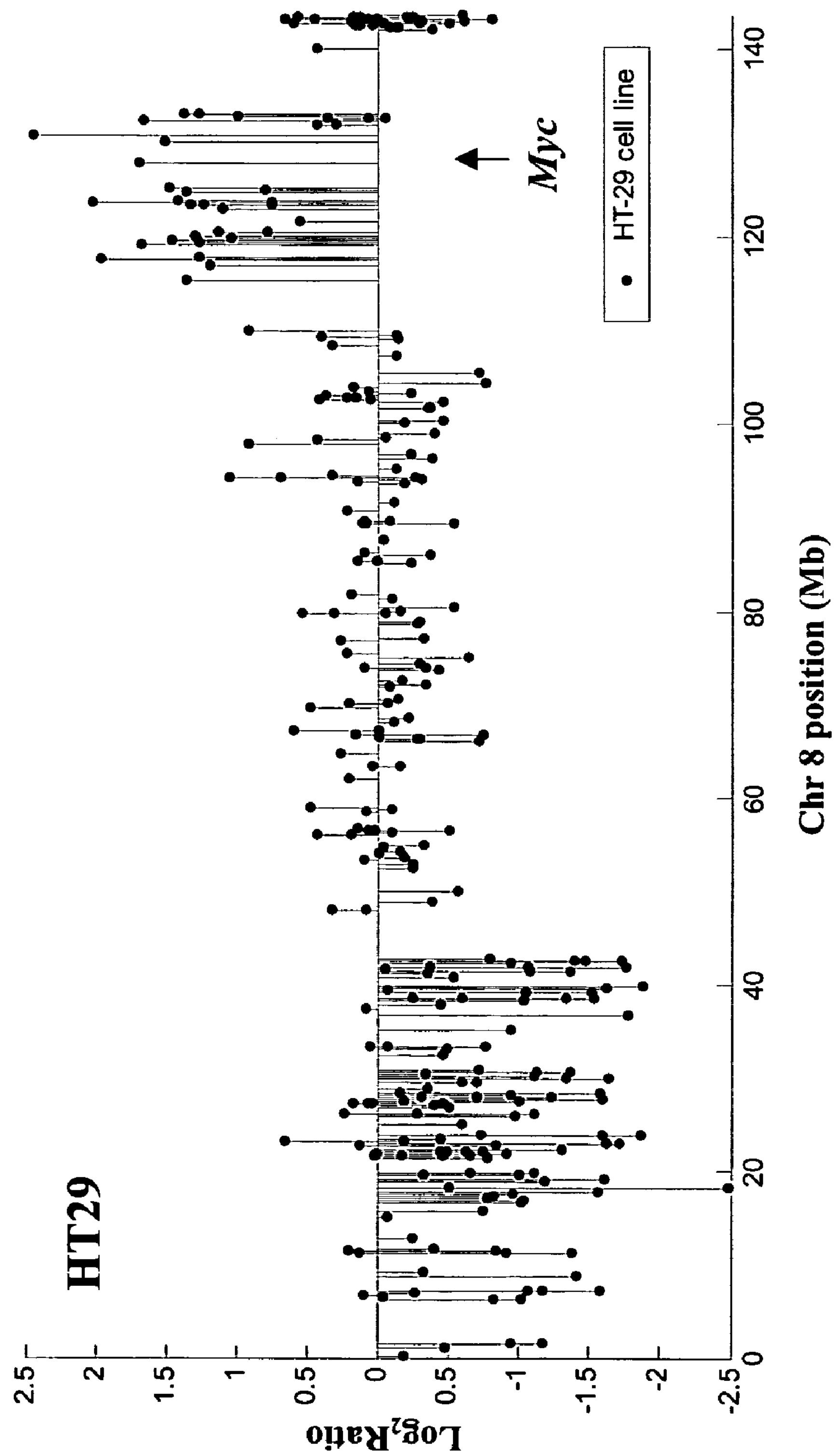

To further characterize the capability of 60-mer oligonucleotide microarrays to detect and map regions of amplification and deletion throughout the genome, a second array (array 2) was used to measure copy number variations in tumor cell lines, including Colo320 and HT−29, with chromosomal abnormalities previously characterized by various technologies including BAC aCGH (Snyijders et al., supra). Array 2 consisted of 60-mer oligonucleotide features designed and validated for expression profiling of more than 17,000 transcripts. Data from 97 features whose reference channel signals were less than 3 standard deviations above the average of 162 negative control feature signal intensities were discarded. In addition 5950 features that contained either homology to more than one genomic sequence (5175 features) or spanned multiple exons (755 features) were removed, leaving 11066 features including 373 on the X chromosome. Previously characterized chromosomal aberrations detected in these cell lines included a high-level ($log_2$ratio=6.4) amplification of MYC in Colo320 (FIG. 4_a_), and an amplicon spanning 8q23.1-q24.23 with a 3-fold ($log_2$ratio=1.5) increase in the copy number of MYC with simultaneous single copy 8p deletion in HT-29 (FIG. 4_b_).

In order to test oligonucleotide aCGH with patient samples, four soft tissue sarcomas collected from 1980-2003 and accessioned via the National Cooperative Human Tissue Network (CHTN) were screened. These were hybridized to Array2 with normal female reference DNA. Amplicons on chromosome 12q that contained known targets of amplification in sarcomas such as SAS, HDM1, and HMGIC were identified in these tumors (Table1).

TABLE 1

Detection of Copy Number Changes in In Vivo Sarcomas

| Feature | | Log$_2$ Fluorescence Ratios[a] Sarcoma Samples | | | |
|---|---|---|---|---|---|
| Gene | Locus | ST103 | ST112 | ST130 | ST240 |
| SAS | 12q13.3 | 0.36 | 3.50 | 2.29 | 1.04 |
| DYRK2 | 12q14.3 | −0.05 | 0.18 | 2.21 | 3.64 |
| HMGIC | 12q14.3 | 0.39 | 2.75 | 3.84 | 1.41 |
| HDM1 | 12q15 | −0.48 | 2.08 | 2.11 | 3.82 |
| IFNG | 12q15 | −0.58 | −1.14 | 0.75 | 3.62 |

[a]Log$_2$ratios of Cy5/Cy3 background subtracted dye normalized fluorescence signals for individual 60-mer fetures that map to the indicated gene locus.

Figure 5:
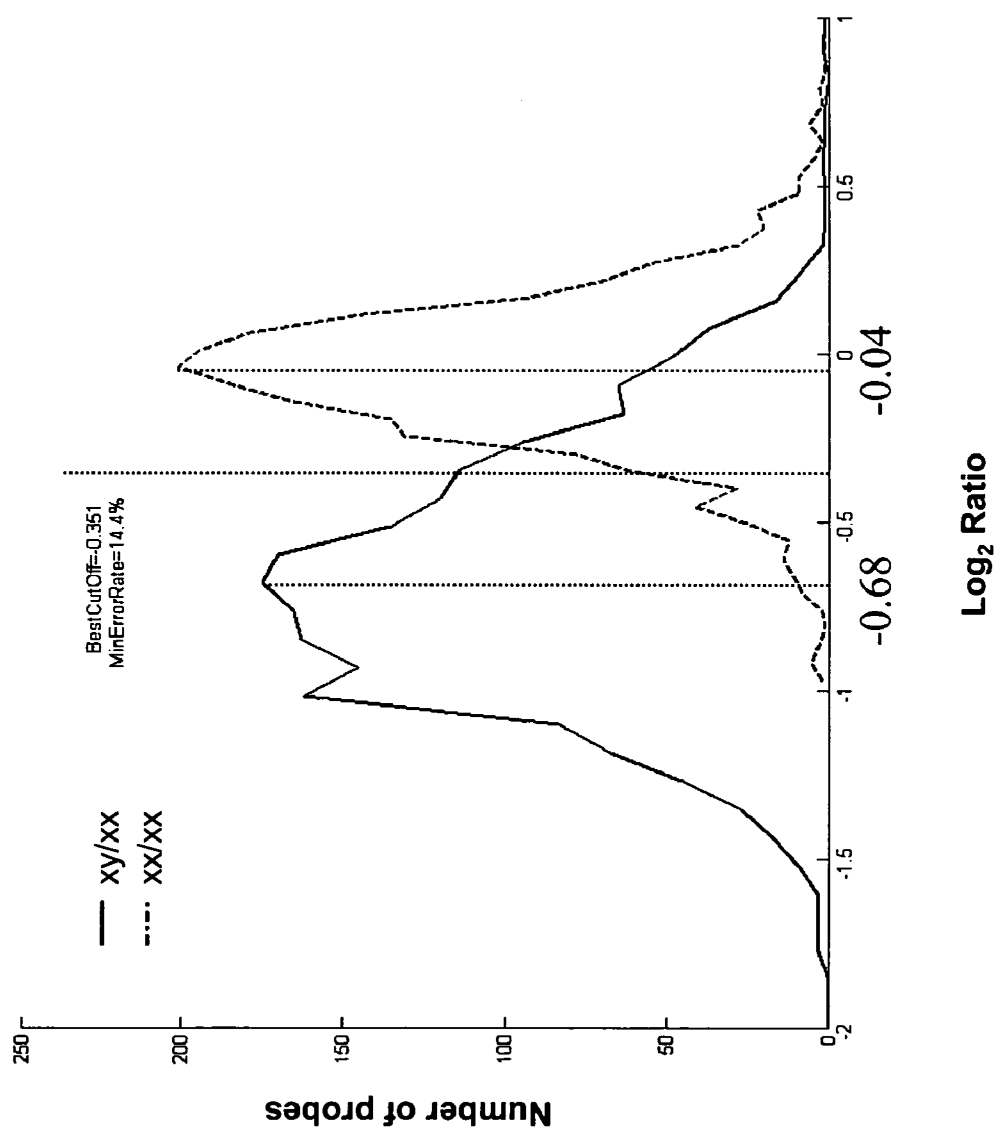
Figure 6:
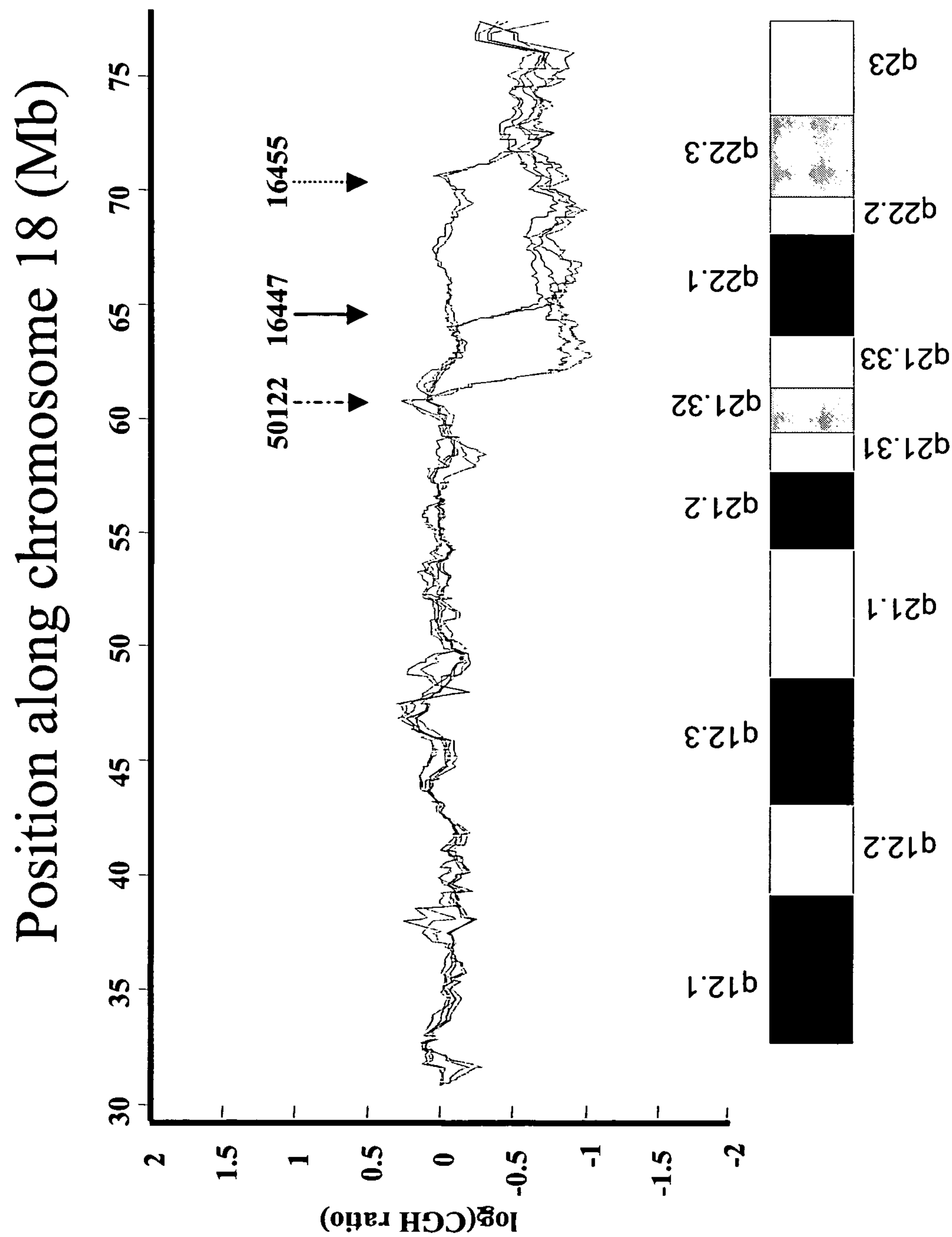
Figure 7:
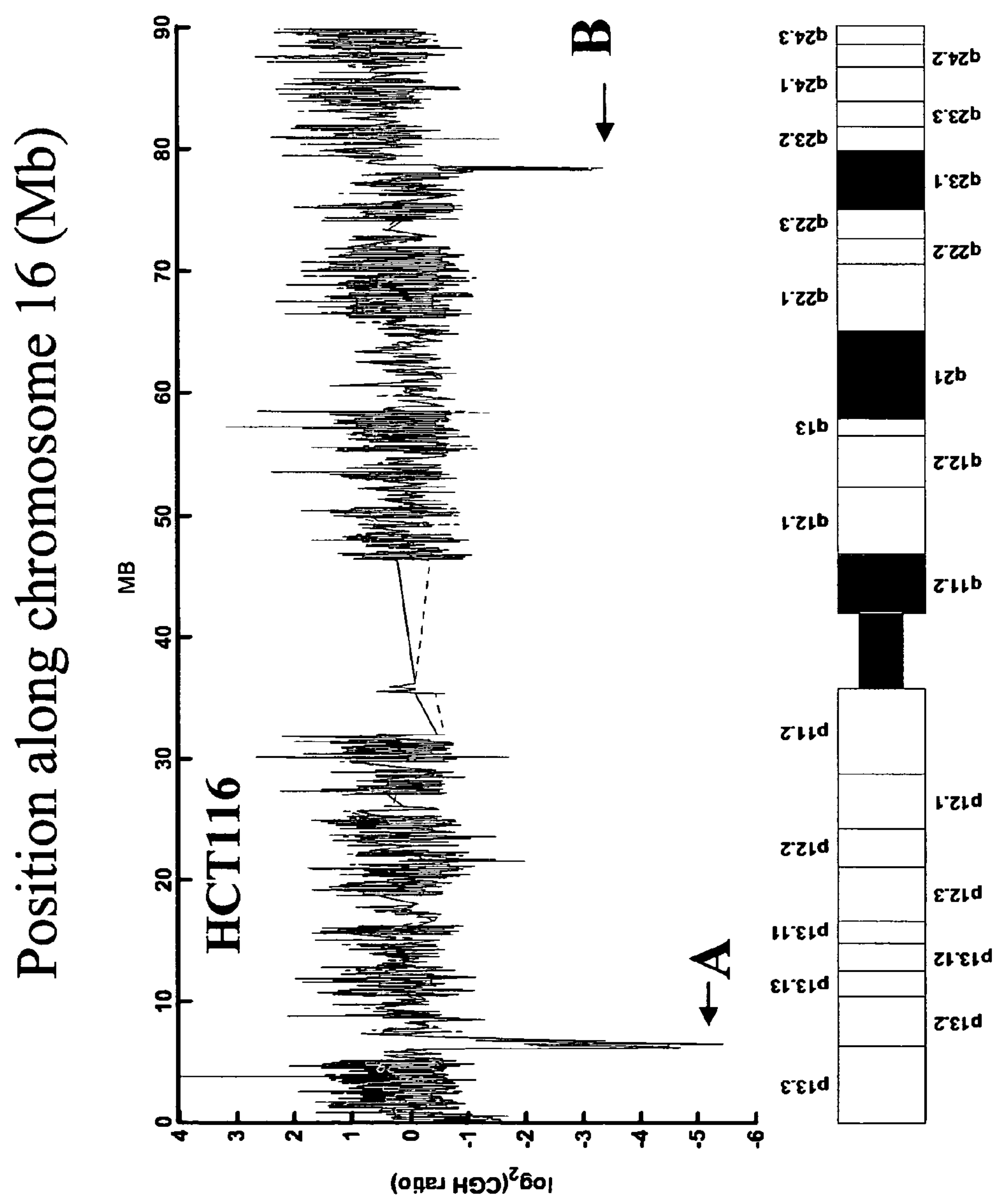

Array 3 contained features representing unique genomic sequences that spanned the X chromosome at an average spacing of 75 kb. These same arrays contained 1653 features representing unique genomic sequences at approximately 50 kb average spacing along chromosome 18q to assess the ability to detect and map intrachromosomal single copy losses in the 18q-syndrome patient derived cell lines. DNA from diploid cell lines derived from 18q-syndrome patients (one XX and three XY) containing cytogenetically mapped deletions of chromosome 18q (U.S. Pat. No. 6,465,182) was cohybridized with normal XX reference DNA to Array 3. For this array 38 of 2116 features from the X chromosome and 14 of 1653 features from 18q were considered insignificant as they had mean signals less than a value of the background level plus three standard deviations of the negative control features in the reference channel in at least 6 of 11 hybridizations. Examination of the ratios of the X chromosome features from duplicate hybridizations from the three XY and one XX 18q-syndrome patients revealed an average median log2 ratio value of −0.68 for XY/XX and −0.04 for XX/XX (FIG. 5). The best threshold between the X chromosome feature ratios that differentiates between XY/XX and XX/XX permits a feature-by-feature call rate for XY versus XX of greater than 85%. In each of these cell lines single copy loss on 18q was detected and the breakpoint region was localized visually and numerically within the known cytogenetic band location (FIG. 6) (Silverman et al., Human Genet. (1995) 56: 926-937). Breakpoints within 120 kb of the initial assays were observed in duplicate hybridizations, indicating a high level of reproducibility. To test our ability to detect and measure homozygous deletions, we utilized Array 4, which contains 5464 features spanning chromosome 16 with feature content biased toward expressed gene regions. We cohybridized to them genomic DNA from the well characterized colon carcinoma cell line HCT116 that contains homozygous deletions at 16p12 and 16q23 (Snijders et al., Nat Genet. (2001) 29(3):p.263-4; Paige et al., Cancer Res. (2000) 60:p1690-7) with normal female DNA (FIG. 7). We observed two regions on chromosome 16 with CGH ratios consistent with areas of homozygous deletion and were able to localize these deletions to single gene loci: 16p12.2 (deletion A) A2BP1; 16q23.1 (deletion B) WWOX.

The above results demonstrate that in situ synthesized 60-mer oligonucleotide arrays can reproducibly detect genomic lesions, including single copy and homozygous deletions, as well as variable amplicons, using whole genomes from a variety of tissue sources as targets. Given the unsurpassed design flexibility inherent in oligonucleotide arrays, the demonstration here that they can be used to characterize copy number abnormalities in non-reduced complexity samples shows that this technology will emerge as a standard tool for research and diagnostics of cancer and genetic disease, among other applications.

II. Materials and Methods

A. Genomic DNA.

Genomic DNA from normal male 46,XY and normal female 46,XX DNA from Promega (Madison Wis.) was obtained. Cell lines: 47,XXX (repository number GM04626), 48,XXXX (GM01415D), 49,XXXXX (GM05009C) and the 18q deletion syndrome cell lines (GM16447, 16449, 16451, 16453,16455, and 50122) are part of the NIGMS Human Genetic Cell Repository and were obtained from the Coriell Institute of Medical Research. The colon carcinoma lines (COLO 320DM, HT 29 and HCT-116) and the breast carcinoma cell lines (MDA-MB-231 and MDA-MB453) were obtained from American Type Culture Collection. Each cell line was grown under conditions specified by the supplier. Genomic DNA was prepared from each cell line using the DNeasy Tissue Kit (Qiagen, Germantown, Md.). Tumor biopsies were collected from 1980-2003, accessioned via the National Cooperative Human Tissue Network (CHTN). Total cellular DNA was isolated from fresh frozen tumor specimens using standard TRIzol Reagent (Invitrogen, Gaithersburg, Md.) extraction techniques and further purified with standard chloroform-phenol extraction techniques.

B. Summary of Arrays 1 to 4

| | Array Design | Number of Relevant Features (60 mers) |
|---|---|---|
| Array 1 | Designed for gene expression | Total: 7900<br>Chromosome X: 273<br>Chromosome Y: 14 |
| Array 2 | Designed for gene expression (Agilent Human 1A Oligo Array) | Total: 17000<br>Chromosome X: 373<br>Chromosome 8: 348<br>Chromosome 12: 399 |
| Array 3 | Custom array design | Total: 22000<br>Chromosome X: 2116<br>Chromosome 18: 1653 |
| Array 4 | Custom array design | Total: 22000<br>Chromosome 16: 5464 |

C. Sample Labeling.

For each CGH hybridization, 20 μg of genomic DNA from the reference (46,XX female) and the corresponding experimental sample with AluI (12.5 units) and RsaI (12.5 units) (Promega) was digested. All digests were done for a minimum of 2 hours at 37° C. then verified by agarose gel analysis. Individual reference and experimental samples were then filtered using the Qiaquick PCR Cleanup Kit (Qiagen). Labeling reactions were performed with 6 μg of purified restricted DNA and a Bioprime labeling kit (Invitrogen) according to the manufacturer's directions in a 50 μl volume with a modified dNTP pool; 120 μM each of dATP, dGTP, dTTP, 60 μM dTTP, and 60 μM of either Cy5-dUTP for the experimental sample or Cy3-dUTP for the 46,XX female reference (Perkin-Elmer, Boston, Mass.). Labeled nucleic acids were subsequently filtered using a Centricon YM-30 filter (Millipore, Bedford, Mass.). Experimental and reference nucleic acids for each hybridization were pooled, mixed with 50 μg of human Cot-1 DNA (Invitrogen), 100 μg of yeast tRNA (Invitrogen) and 1X hybridization control nucleic acids (SP310, Operon). The nucleic acid mixture was purified then concentrated with a Centricon YM-30 column, and resuspended to a final volume of 250 μl, then mixed with an equal volume of Agilent 2X in situ Hybridization Buffer.

D. Oligonucleotide Microarray Processing.

Prior to hybridization to the arrays, the 500 μl hybridization mixtures were denatured at 100° C. for 1.5 minutes and incubated at 37° C. for 30 minutes. In order to remove any precipitate, the mixture was centrifuged at ≧14,000 g for 5 minutes and transferred to a new tube leaving a small residual volume (≦5 μl). The sample was applied to the array using an Agilent microarray hybridization chamber and hybridization was carried out for 14-18 hrs at 65° C. in a Robbins Scientific rotating oven at 4 rpm. The arrays were then disassembled in 0.5×SSC/0.005% Triton X102 (wash 1) at 65° C. then washed for 10 minutes at RT in wash 1, followed by 5 minutes at RT in 0.1×SSC/0.005% Triton X102 (wash 2). Slides were dried and scanned using an Agilent 2565AA DNA microarray scanner.

E. Image and Data Analysis.

Microarray images were analyzed using Agilent Feature Extraction software version 6.1.1. Default settings were used except that only 60-mer features from diploid autosomal chromosomes were used for dye normalization using the locally weighted linear regression curve fit (LOWESS) method (http://www.chem.agilent.com/temp/rad506EE/00036948.pdf.). Arrays 2,3 and 4 contained replicate features for a subset of the feature sequences. For these replicate features the mean and standard deviation of background-subtracted signals was calculated in both channels independently after the elimination of outliers. Outlier feature rejection was based on limits of 1.5 IQR (intraquartile ranges) from the median.

The above results and discussion demonstrate that novel methods of performing CGH are provided. Advantages of the subject invention that result from the use of immobilized oligonucleotide features include, but are not limited to: (a) the ability to employ short feature oligonulceotides that minimize cross-hybridization while maintaining maximum hybridization affinity; (b) lower background and therefore a lower limit of detection; (c) increased resolution for both coding and a non-coding regions; (d) elimination of need to screen or assay nucleic acid collections of reduced complexity, (and therefore the elimination of the need to employ protocols that reduce complexity, e.g., by selective amplification, with their attendant possibilities of undesired selective enhancement; (e) the ability to detect DNA alterations at virtually any site in the genome; and the like. As such, the subject methods represent a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for comparing the copy number of at least one nucleic acid sequence in at least two genomic sources, said method comprising:

(a) preparing at least a first collection of nucleic acid molecules from a first genomic source and a second collection of nucleic acid molecules from a second genomic source, wherein said first and second genomic sources have a complexity of $1\times10^8$ base pairs or more and said first and second collections are of non-reduced complexity;

(b) contacting said first and second collections of nucleic acid molecules with one or more pluralities of distinct oligonucleotide feature elements bound to a surface of a solid support, wherein said one or more pluralities of distinct oligonucleotide feature elements each consists essentially of oligonucleotide feature nucleic acids that range in size from 20 nt to 200 nt in length and said contacting occurs under stringent assay conditions;

(c) measuring the binding of the first and second collections of nucleic acid molecules to said feature elements to produce data; and (d) identifying a quantitative difference in the copy number of at least one nucleic acid sequence in said at least two genomic sources using said data

2. The method according to claim 1, wherein said oligonucleotide feature nucleic acids range in size from 20 to 100 nt in length.

3. The method according to claim 2, wherein said oligonucleotide feature nucleic acids range in size from 40 to 80 nt in length.

4. The method according to claim 1, wherein said plurality of oligonucleotide feature elements bound to a surface of a solid support includes sequences representative of locations distributed across at least a portion of a genome.

5. The method according to claim 4, wherein said locations have a uniform spacing across at least a portion of a genome.

6. The method according to claim 4, wherein said locations have a non-uniform spacing across at least a portion of a genome.

7. The method according to claim 1, wherein said plurality of oligonucleotide feature elements bound to a surface of a solid support samples a genome at least every 20 Kb.

8. The method according to claim 1, wherein said plurality of oligonucleotide feature elements bound to a surface of a solid support samples at least a portion of the genome at least every 2 Kb.

9. The method according to claim 1, wherein said nucleic acids of said first and second collections range in length from 100 to 10000 nt in length.

10. The method according to claim 9, wherein said nucleic acids of said first and second collection range in length from 100 to 500 nt in length.

11. The method according to claim 1, wherein said collections of nucleic acids are contacted with the same plurality of distinct oligonucleotide feature elements.

12. The method according to claim 11, wherein said collections of nucleic acids are distinguishably labeled.

13. The method according to claim 1, wherein said first collection of nucleic acid molecules is contacted with a first array comprising a plurality of distinct oligonucleotide feature elements and said second collection is contacted with a second array comprising a plurality of distinct oligonucleotide feature elements that is substantially identical to that of said first array.

14. The method according to claim 1, wherein said one or more pluralities of distinct oligonucleotide feature elements comprises distinct oligonucleotide feature elements that correspond to non-coding genomic regions.

15. The method according to claim 1, wherein said one or more pluralities of distinct oligonucleotide feature elements comprises distinct oligonucleotide feature elements that correspond to coding genomic regions.

16. The method according to claim 1, wherein the solid support is a planar substrate.

17. The method according to claim 16, wherein said planar substrate is glass.

18. The method according to claim 1, wherein said non-reduced complexity collections have a complexity that is at least 10% of their genomic sources.

19. The method according to claim 1, wherein said non-reduced complexity collections have a complexity that is at least 25% of their genomic sources.

20. The method according to claim 1, wherein said non-reduced complexity collections have a complexity that is at least 50% of their genomic sources.

21. The method of claim 1, wherein said plurality of distinct oligonucleotide feature elements bound to a solid surface comprises an array.

22. The method according to claim 1, further comprising reiterating steps (a) to (c) using a second plurality of distinct oligonucleotide feature elements bound to a surface of a solid support that more frequently samples a reduced region of the genome as compared to a prior iteration.

23. The method according to claim 1, wherein said method further comprises a data transmission step in which a result from said evaluating is transmitted from a first location to a second location.

24. The method according to claim 23, wherein said second location is a remote location.

25. The method according to claim 1, wherein each of said first and second collections is prepared by a primer extension reaction using a set of random primers and using said genomic sources as genomic templates.

26. The method according to claim 25, wherein said set of primers is made up of primers having a length Y and the total number of different primer sequences present in said set is $4^Y$.

27. The method according to claim 26, wherein Y ranges from 3 to 25.

28. The method according to claim 1, wherein said support comprises hydrophilic, high surface energy feature regions and hydrophobic, low surface energy interfeature regions.

29. The method according to claim 1, wherein said method is capable of detecting a one copy deletion between said first and second collections of nucleic acids using 20 μg of genomic DNA for a genomic source.

30. The method according to claim 1, wherein said contacting step (b) comprises rotating the array during hybridization.

31. The method according to claim 1, wherein said first sample consists essentially of at least a first collection of nucleic acid molecules from a first genomic source and said second sample consists essentially of a second collection of nucleic acid molecules from a second genomic source.

32. The method according to claim 1, wherein said oligonucleotide feature elements bound to a surface of a solid support are fabricated in situ on said surface.

33. The method according to claim 1, wherein said preparing comprises amplifying said first genomic source and second genomic source in a manner such that said first and second collections are of non-reduced complexity.

34. The method according to claim 1, wherein said first and second genomic sources are obtained from a metazoan organism.

35. The method according to claim 34, wherein said metazoan organism is a mammalian organism.

36. The method according to claim 1, wherein said first and second genomic sources are obtained from a plant.

37. The method according to claim 1, wherein said first and second genomic sources are obtained from an animal.

38. The method according to claim 1, wherein said one or more pluralities of distinct oligonucleotide feature elements are bound to the same surface of a solid support.

39. The method according to claim 1, wherein step (d) comprises identifying a single copy number heterozygous deletion in a genomic region of said first or second genomic sources.

40. The method according to claim 1, wherein said genomic region is a whole chromosome.

41. The method to claim 1 wherein said genomic region is a portion of a chromosome.

42. The method of claim 1, wherein said first and second genomic sources comprise human genomic DNA.

* * * * *

UNITED STATES PATENT AND TRADEMARK OFFICE

CERTIFICATE OF CORRECTION

PATENT NO. : 8,232,055 B2
APPLICATION NO. : 10/744595
DATED : July 31, 2012
INVENTOR(S) : Laurakay Bruhn et al.

It is certified that error appears in the above-identified patent and that said Letters Patent is hereby corrected as shown below:

On the face page, in field (56), under "Other Publications", in column 2, line 7, delete "Winzeler al." and insert -- Winzeler et al. --, therefor.

On the face page, in field (56), under "Other Publications", in column 2, line 12, delete "Cytogenic Analysos" and insert -- Cytogenetic Analysis --, therefor.

In column 25, line 15, in Claim 1, after "data" insert -- . --.

In column 28, line 1, in Claim 41, after "method" insert -- according --.

Signed and Sealed this
Fifth Day of February, 2013

Teresa Stanek Rea
*Acting Director of the United States Patent and Trademark Office*